United States Patent
Schulte et al.

(10) Patent No.: US 6,379,514 B1
(45) Date of Patent: Apr. 30, 2002

(54) COMPOSITION STRUCTURE FOR $NO_x$ SENSORS

(75) Inventors: Thomas Schulte, Stuttgart; Thomas Wahl, Pforzheim; Bernd Schumann, Rutesheim; Reiner Schuetz, Ditzingen; Rainer Waser, Aachen, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/529,505

(22) PCT Filed: Oct. 14, 1998

(86) PCT No.: PCT/DE98/03005

§ 371 Date: Sep. 28, 2000

§ 102(e) Date: Sep. 28, 2000

(87) PCT Pub. No.: WO99/19721

PCT Pub. Date: Apr. 22, 1999

(30) Foreign Application Priority Data

Oct. 14, 1997 (DE) .......................... 197 45 328

(51) Int. Cl.⁷ ............................................ G01N 27/407
(52) U.S. Cl. .................. 204/429; 96/4; 96/7; 96/9; 96/11; 204/424; 204/426; 205/781
(58) Field of Search ................ 204/421–429; 96/4, 7, 9, 11

(56) References Cited

U.S. PATENT DOCUMENTS

| 5,543,025 A |   | 8/1996  | Garzon et al.   |
|-------------|---|---------|-----------------|
| 5,681,373 A | * | 10/1997 | Taylor et al.   |
| 5,723,035 A | * | 3/1998  | Mazanee et al.  |
| 5,866,799 A | * | 2/1999  | Kato et al.     |
| 5,902,379 A | * | 5/1999  | Phillips et al. |
| 6,143,159 A | * | 11/2000 | Bloomfield      |

FOREIGN PATENT DOCUMENTS

| DE | 44 39 901  | 5/1996 |
| DE | 196 52 968 | 3/1998 |
| EP | 0 468 500  | 1/1992 |

OTHER PUBLICATIONS

"Thick Film $ZrO_2$ $NO_x$ Sensor," Kato et al., SAE, pp. 137–142 (1996), month unavailable.

* cited by examiner

Primary Examiner—T. Tung
(74) Attorney, Agent, or Firm—Kenyon & Kenyon

(57) ABSTRACT

A structural arrangement for $NO_x$ sensors including a first selectively oxygen ion-conductive layer and a second gas-permeable, nonconductive layer, the latter having a porous spinel structure or porous platinum. The oxygen ion-conductive layer made from a mixed-conductive ceramic can have an additional layer of a material which is catalytically inactive to $NO_x$.

6 Claims, 1 Drawing Sheet

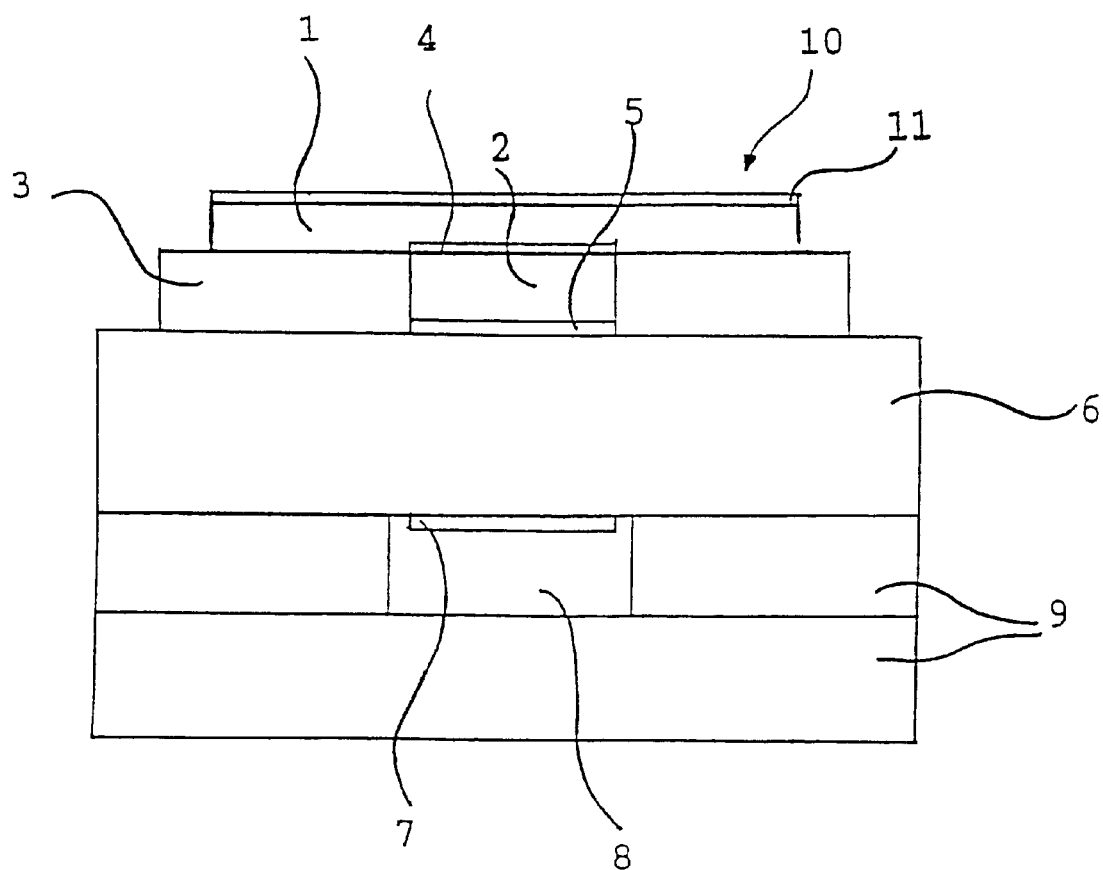

COMPOSITION STRUCTURE FOR $NO_x$ SENSORS

FIELD OF THE INVENTION

The invention relates to a structural arrangement for $NO_x$ sensors including a first selectively oxygen ion-conductive layer and a second gas-permeable nonconductive layer.

BACKGROUND INFORMATION

It is known that exhaust gases of internal combustion engines, lean mixture engines in particular, contain nitrogen oxides and other gases in addition to unburned fuel components and oxygen. The composition of the exhaust gas is essentially determined by the setting of the air-fuel mixture with which the internal combustion engine is operated. If, for example, fuel is present in excess of a stoichiometric mixture, considerable amounts of unburned or only partially burned fuel are present in the exhaust gas while oxygen in excess of a stoichiometric mixture of the air in the air-fuel mixture results in a correspondingly higher concentration of oxygen in the exhaust gas. A known method for setting an optimum air-fuel mixture is to determine the composition of the exhaust gas in a proportional probe. In doing so, the limiting current probe has a solid electrolyte arranged between two electrodes, one electrode being exposed to the exhaust gas via a diffusion barrier. With a constant voltage applied to the electrodes, a limiting current occurs on both electrodes due to a difference in oxygen concentration, the limiting current being measured by a measuring device and analyzed, for example, for setting the air-fuel mixture with which the internal combustion engine is operated.

One possibility for determining oxygen and nitrogen oxides in particular in gas mixtures is described in the article by N. Kato, K. Nagakaki and N. Ina, SAE 1996, pages 137 to 142. The reactivity of the nitrogen oxides and other gas components with parts of the electrode is regarded as one of the disadvantages of the method described in that article.

Moreover, unpublished German Patent Application No. 196 35 494.3 (equivalent to German Published Patent Application No. 196 52 968) describes a measuring arrangement for the determination of gas components in gas mixtures with at least one electrochemical solid electrolyte measurement cell and at least one cathode exposed to the gas mixture to be measured, the cathode being spatially separated from a layer that selectively conducts oxygen ions by an electrically nonconductive layer which is gas-permeable at least in areas.

Consistent with this patent application, a mixed-conductive ceramic membrane with catalytic inactivity to nitrogen oxides and electrically insulated via a solid electrolyte pump cell must be provided for the structure of an amperometric $NO_x$ sensor. The ceramics used for this purpose may be composed of a metallic oxide, with perovskite ceramics being used frequently.

Previously, the mixed-conductive ceramics were imprinted onto a porous $Al_2O_3$ structure as a support material. In this process, several components of the metallic oxide ceramic diffused into the $Al_2O_3$ structure and formed phases with a spinel structure at the boundary surface of the membrane, with these phases being nonconductive to poorly conductive for ions.

An additional problem was that the ceramic materials known to be outstandingly mixed-conductive have as a rule, however, a highly catalytic activity toward $NO_x$. On the other hand, the materials that are inactive to $NO_x$, nickel catalyst materials, show only a slight resultant oxygen permeation rate.

SUMMARY OF THE INVENTION

An object of the present invention is to make a structural arrangement for $NO_x$ sensors available in which the supporting material does not substantially inhibit the exchange of oxygen into the gas phase and does not influence the structure of the mixed-conductive ceramic and accordingly the ionic conductivity. Moreover, the mixed-conductive membrane should have a high electron and ion conductivity, resulting in high oxygen permeability while at the same time, however, the catalytic activity to $NO_x$ should be as low as possible.

The object is achieved according to the present invention by a structural arrangement for $NO_x$ sensors which includes a first selectively oxygen ion-conductive layer and a second gas-permeable, nonconductive layer which has a porous spinel structure or porous platinum.

Spinels are understood to be a group of minerals and synthetically produced materials having the general formula $AB_2X_4$, A signifying a bivalent metal, B a trivalent or quadrivalent metal and X=O, S, Se. $Al_2O_3$. MgO and/or $Co_3O_4$ may be used as particularly preferred spinels. The use of spinels according to the present invention possibly increases the standard reaction enthalpy for the formation of products from mixed-conductive perovskites and from the spinel substrate structure in relation to the previously used $Al_2O_3$ substrates. It might thus be possible to inhibit the formation of nonconductive boundary phases.

Platinum substrates may be used in the production of the mixed-conductive layer. In doing so, no reaction takes place between the substrate and the ceramic. However, the porous platinum ensures a good bond between the substrate and the mixed-conductive layer.

In one embodiment of the present invention, the structural arrangement is characterized in that the selectively oxygen ion-conductive layer is made from a mixed-conductive ceramic having a layer on the side facing the exhaust gas which is made from a material that is catalytically inactive to $NO_x$.

Examples of suitable materials that are catalytically inactive to $NO_x$ are $Gd_{0.7}Ca_{0.3}CoO_{3-\delta}$, $Gd_{0.7}Ca_{0.3}FeO_{3-\delta}$, composite materials of mixtures of $Ce_{0.8}Gd_{0.2}O_{2-\delta}$ and $Gd_{0.7}Ca_{0.3}CoO_{3-\delta}$.

This layer can be applied to the layer composed of a mixed-conductive ceramic with the aid of thick-film technology or by a vapor deposition method.

In doing so, the layer is of a nickel catalyst material which is at least more than one layer of atoms thick, the nickel catalyst material rendering the mixed-conductive ceramic membrane inactive on its channel-side surface. The high ionic conductivity of the oxygen through the ceramic material is preserved in this manner.

In a preferred embodiment the mixed-conductive ceramic is composed of a perovskite or elpasolite, in particular having the composition $Ca_{0.7}Sr_{0.7}CoO_{3-\delta}$ or $SrFeCo_{0.5}O_{3-\delta}$.

According to the present invention, the range of variation of the mixed-conductive membrane materials suitable for use is now significantly and advantageously expanded by the modification of the substrate structure. Thus the elimination of the previous inactivation of the boundary surface distinctly reduces the permeability of the membrane with constant effective permeation quantity per surface area. Also, the entire membrane surface can be substantially reduced by the novel structural arrangement since the permeation through the ceramic material is substantially increased with continued catalytic inactivity of the surface.

Thus according to the present invention, the sensor diffusion distance is reduced and the response time of the sensor is reduced accordingly.

It is therefore now possible in an advantageous manner to extend the measuring range of the sensor with regard to the $O_2/NO_x$ proportion with the same membrane surface.

Moreover, the contamination of the surface advantageously results in a reduction and inhibition of aging and drift phenomena, respectively, in the ceramic membrane.

With constant oversizing of the membrane surface, which is at least required for the complete oxygen removal, the total increased permeation per surface area now makes it possible for a larger proportion of surface area to be contaminated without disadvantageously influencing the characteristics of the sensor.

BRIEF DESCRIPTION OF THE DRAWING

The FIGURE shows a measuring arrangement and structural arrangement according to the present invention.

DETAILED DESCRIPTION

The FIGURE shows a measuring arrangement which is generally identified as 10. This measuring arrangement 10 has a solid electrolyte 6 essentially in the form of a sheet on the side of which is arranged an electrode which is connected as an anode 7. An electrode connected as a cathode 5 is arranged on the side of solid electrolyte 6 opposite anode 7, the electrolyte being made from, for example, a zirconium dioxide-yttrium oxide ceramic. Cathode 5 is partially covered with a gastight layer 3, for example of α- or γ-aluminum oxide or a layer of purely ion conductive material. It borders gas-permeable, nonconductive layer 2 which has a porous spinel structure. These electrically insulating layers 2, 3 are covered with an additional layer 1 which is composed of a mixed-conductive metal oxide ceramic. This forms a selectively oxygen ion-conductive layer. The thickness of this layer varies between 5 and 200 μm. The boundary surface of mixed-conductive ceramic membrane 1 with nonconductive layer 2 is identified as 4. Layer 11 which is catalytically inactive to $NO_x$ is present on mixed-conductive ceramic membrane 1. Both anode 7 as well as the cathode are connected to measuring arrangement 10 via conductors with terminals, both of which are not shown here. Electrodes 5, 7 are preferably made of platinum or another corrosion-resistant metal or metal alloy. A diffusion channel 8 is arranged beneath anode 7, via which reference air can be directed to anode 7. Diffusion channel 8 for the reference air is accommodated in a multilayer body 9 which is built up from multiple layers, multilayer body 9 being made from zirconium dioxide, for example.

What is claimed is:

1. A structural arrangement for an $NO_x$ sensor, comprising:
    a first selectively oxygen ion-conductive layer made of a mixed-conductive ceramic including a layer on a side facing an exhaust gas and formed from a material that is catalytically inactive to $NO_x$; and
    a second gas-permeable, nonconductive layer including a porous spinel structure.

2. The structural arrangement according to claim 1, wherein:
    the mixed-conductive ceramic includes one of a perovskite and elpasolite.

3. The structural arrangement according to claim 2, wherein:
    the mixed-conductive ceramic includes one of $Ca_{0.7}Sr_{0.7}CoO_{3-\delta}$ and $SrFeCo_{0.5}O_{3-\delta}$.

4. The structural arrangement according to claim 1, wherein:
    the porous spinel structure includes at least one of $Al_2O_3 \cdot MgO$ and $Co_3O_4$.

5. The structural arrangement according to claim 1, wherein:
    the material that is catalytically inactive to NOx is applied to the first selectively oxygen ion-conductive layer by an implementation of one of a thick-film technology and a vapor deposition operation.

6. A measuring arrangement for a $NO_x$ sensor, comprising:
    a cathode; and
    a structural arrangement arranged over the cathode, the structural arrangement including:
        a first selectively oxygen ion-conductive layer made a mixed-conductive ceramic including a layer on a side facing an exhaust gas and formed from a material that is catalytically inactive to NOx, and
        a second gas-permeable, nonconductive layer including a porous spinel structure.

* * * * *